United States Patent
Wu et al.

(10) Patent No.: US 8,571,645 B2
(45) Date of Patent: Oct. 29, 2013

(54) SYSTEM AND METHOD FOR EVALUATING CARDIOVASCULAR PERFORMANCE IN REAL TIME AND CHARACTERIZED BY CONVERSION OF SURFACE POTENTIAL INTO MULTI-CHANNELS

(75) Inventors: Chau-Chung Wu, Taipei (TW);
Chii-Wann Lin, Taipei (TW);
Chien-Sheng Liu, Taichung (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 13/445,985

(22) Filed: Apr. 13, 2012

(65) Prior Publication Data
US 2013/0158421 A1    Jun. 20, 2013

(30) Foreign Application Priority Data
Dec. 20, 2011 (TW) .............................. 100147510 A

(51) Int. Cl.
*A61B 5/0402* (2006.01)

(52) U.S. Cl.
USPC ........................... 600/516; 600/515; 600/517

(58) Field of Classification Search
USPC ......................... 600/515, 516, 517
See application file for complete search history.

(56) References Cited

U.S. PATENT DOCUMENTS

| 6,308,094 B1* | 10/2001 | Shusterman et al. | 600/516 |
| 2007/0203418 A1* | 8/2007 | Starc | 600/509 |
| 2008/0114257 A1* | 5/2008 | Molin et al. | 600/512 |
| 2010/0217144 A1* | 8/2010 | Brian | 600/523 |

* cited by examiner

*Primary Examiner* — Joseph Dietrich
(74) *Attorney, Agent, or Firm* — Schmeiser, Olsen & Watts, LLP

(57) ABSTRACT

A system and method for evaluating cardiovascular performance in real time and characterized by conversion of a surface potential into multi-channels are introduced. The system includes an electrocardiographic signal measuring unit, a reconstruction unit, and a parameter computation and assessment unit. The reconstruction unit reconstructs electrocardiographic signals (ECG signals) recorded by the electrocardiographic signal measuring unit, such that the ECG signals are reconstructed as ones located at different spatial positions but actually not having a channel. The method includes calculating a variation manifested spatially during an interval between a Q wave and a T wave of an ECG signal against time with a parameter computation and assessment algorithm, to evaluate its discreteness degree and thereby diagnose cardiovascular diseases (CVD) and locate lesions thereof.

14 Claims, 6 Drawing Sheets

SYSTEM AND METHOD FOR EVALUATING CARDIOVASCULAR PERFORMANCE IN REAL TIME AND CHARACTERIZED BY CONVERSION OF SURFACE POTENTIAL INTO MULTI-CHANNELS

FIELD OF TECHNOLOGY

The present invention relates to a system and method for evaluating cardiovascular performance in real time and characterized by the conversion of a surface potential into multi-channels, the reconstruction of electrocardiographic signals (ECG signals) with a reconstruction algorithm, and the calculation of the degree of discreteness of the ECG signals with a parameter computation and assessment algorithm.

BACKGROUND

Among cardiovascular diseases (CVD), coronary artery disease (CAD) is regarded as the main cause of a sudden death. The pathological changes caused by coronary artery disease (CAD) include stenosis and even occlusion of coronary arteries for supplying oxygen and nutrients to the heart, thereby damaging cardiac tissues. Depending on the degree of severity, coronary artery disease (CAD) has different manifestations, namely angina, myocardial infarction, and sudden cardiac death. Angina is chest pain due to ischemia (a lack of blood, thus a lack of oxygen supply) of the heart muscle and typically occurs when the weather is cold or when the patient is mentally or physically overburdened or has an overstretched stomach. Myocardial infarction is worse than angina, because the underlying pathological change typical of myocardial infarction is irreversible damage of the heart muscle. Myocardial infarction ends up in a heart failure, when it is severe. In a worst-case scenario, the consequence of myocardial infarction is a sudden cardiac death, wherein the victim goes into shock and dies as soon as arrhythmia halts the heart and decreases the cardiac output greatly. Hence, coronary artery disease (CAD) is dubbed an invisible killer because of its symptomless insidious course. Coronary artery disease (CAD) is seldom diagnosed with a static electrocardiogram (static ECG), as it starts to alert a patient only when cardiac hypoxia happens to the patient.

At present, diagnosis tools in wide use for diagnosing coronary artery disease (CAD) include treadmill ECG, Thallium scan, and CT-angio. However, the application of the aforesaid diagnosis tools is limited by size, costs, and methodology of measurement, regardless of whether the diagnosis tools are used at hospital or at home. In this regard, the prognosis of coronary artery disease (CAD) is often evaluated by means of conventional ECG signals, albeit with a drawback—providing just 12 channels which are restricted to longitudinal cross-sections and transverse cross-sections of the heart. Although the equipment required for providing the 12-channel ECG signals is simple and easy to operate, its spatial resolution is inadequate, not to mention that it provides a limited amount of information pertaining to the analysis and identification of related symptoms, thereby restricting its application and analysis. Furthermore, although high-resolution magnetocardiography (MCG) provides sufficient spatial information, it is not in wide use because of its high prices and large size.

SUMMARY

It is an objective of the present invention to increase spatial resolution of ECG signals, cut device-related costs, and downsize related devices by measuring multi-channel electrocardiographic signals (ECG signals) and reconstructing multi-dimensional mapping and by making reference to the results of research on the application of magnetocardiography (MCG) in coronary artery disease (CAD).

Another objective of the present invention is to develop a system for evaluating cardiovascular performance in real time and characterized by conversion of a surface potential into multi-channels, wherein the system operates in conjunction with an algorithm that proves effective in performing MCG-based verification.

Yet another objective of the present invention is to develop a system for evaluating cardiovascular performance in real time and characterized by conversion of a surface potential into multi-channels, wherein the system is not only portable and free of radioactivity, but also enables real-time analysis and early prediction.

In order to achieve the above and other objectives, the first aspect of the present invention provides a system for evaluating cardiovascular performance in real time and characterized by conversion of a surface potential into multi-channels. The system comprises: an electrocardiographic signal measuring unit comprising at least one channel located at different spatial positions, the electrocardiographic signal measuring unit recording electrocardiographic signals (ECG signals) measured with the channels, the ECG signals each comprising a P wave, a Q wave, a R wave, a S wave, and a T wave; a reconstruction unit electrically connected to the electrocardiographic signal measuring unit, the reconstruction unit having a reconstruction algorithm for calculating eigenvectors of the ECG signals and using the eigenvectors as a base for calculating an eigenvalue matrix, the reconstruction unit calculating at least one reconstructed ECG signal at other different spatial positions with the eigenvalue matrix and the ECG signals of the channels, the at least one reconstructed ECG signal comprising a reconstructed P wave, a reconstructed Q wave, a reconstructed R wave, a reconstructed S wave, and a reconstructed T wave; and a parameter computation and assessment unit electrically connected to the reconstruction unit and having a parameter computation and assessment algorithm, wherein the parameter computation and assessment unit receives the ECG signals and the at least one reconstructed ECG signal, calculates an interval from a starting point of the Q wave to an ending point of the T wave of the ECG signals, calculates variation in a reconstruction interval from a starting point of the reconstructed Q wave to an ending point of the reconstructed T wave of the at least one reconstructed ECG signal against time at different spatial positions, and evaluates the degree of discreteness of the ECG signals and the at least one reconstructed ECG signal with the parameter computation and assessment algorithm.

The second aspect of the present invention provides a method for evaluating cardiovascular performance in real time and characterized by conversion of a surface potential into multi-channels. The method comprising the steps of: measuring, by the electrocardiographic signal measuring unit, electrocardiographic signals (ECG signals) at different spatial positions with at least one channel, the ECG signals each comprising a P wave, a Q wave, a R wave, a S wave, and a T wave; calculating, by a reconstruction unit, eigenvectors of the ECG signals with a reconstruction algorithm, an eigenvalue matrix with the eigenvectors being used as a base, and at least one reconstructed ECG signal at other different spatial positions with the eigenvalue matrix and the ECG signals of the channels, the at least one reconstructed ECG signal comprising a reconstructed P wave, a reconstructed Q wave, a reconstructed R wave, a reconstructed S wave, and a reconstructed T wave; and receiving the ECG signals and the at least one reconstructed ECG signal by a parameter computation and assessment unit, calculating an interval from a starting point of the Q wave to an ending point of the T wave of the ECG signals, calculating variation in a reconstruction interval from a starting point of a reconstructed Q wave to an ending point of a reconstructed T wave of the at least one reconstructed ECG signal against time at different spatial positions, and evaluating a degree of discreteness of the at least one reconstructed ECG signal and the ECG signals with the parameter computation and assessment algorithm.

BRIEF DESCRIPTION

DETAILED DESCRIPTION

Figure 1:
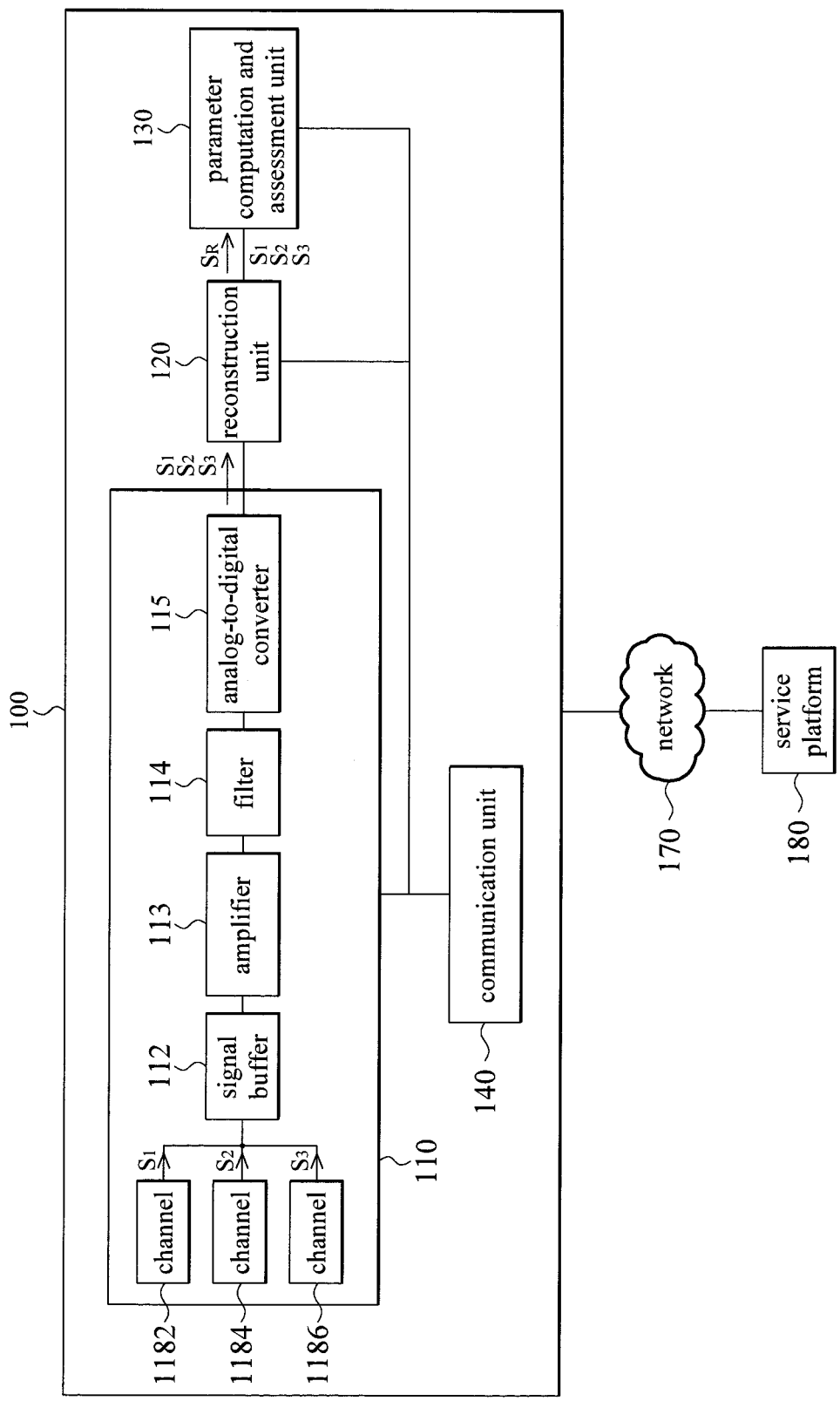
FIG. 1 is a block diagram of a system according to an embodiment of the present invention.

Referring to FIG. 1, there is shown a block diagram of a system 100 for evaluating cardiovascular performance in real time according to the first aspect of the present invention. As shown in FIG. 1, the system 100 for evaluating cardiovascular performance in real time comprises an electrocardiographic signal measuring unit 110, a reconstruction unit 120, and a parameter computation and assessment unit 130. As shown in FIG. 1, for an illustrative purpose, the electrocardiographic signal measuring unit 110 comprises three channels 1182, 1184, 1186. The quantity of the channels is subject to changes. For example, the electrocardiographic signal measuring unit 110 can comprise 12 channels.

Figure 2:
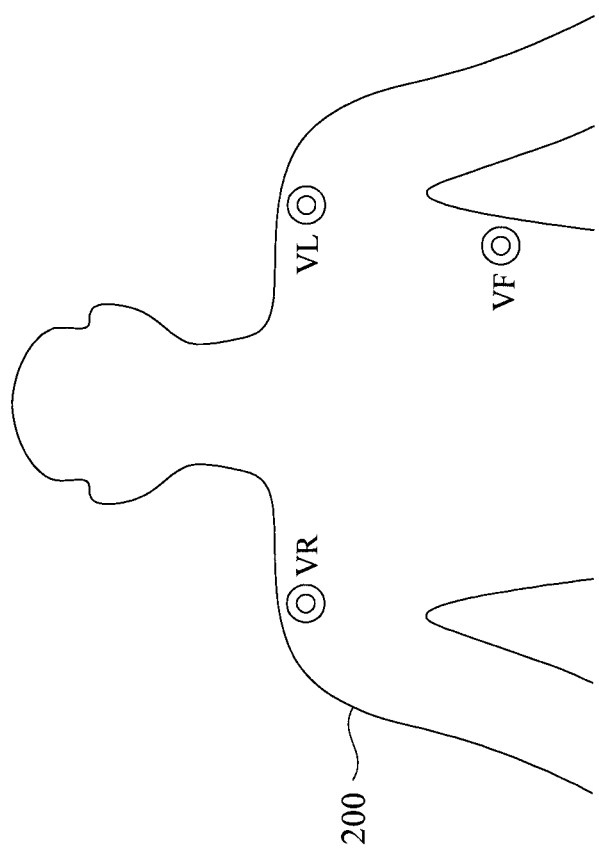
FIG. 2 is a schematic view of the positions of multi-channel electrodes according to an embodiment of the present invention.

Referring to FIG. 2, there is shown a schematic view of the positions of multi-channel electrodes according to an embodiment of the present invention. As shown in the diagram, electrodes VR, VL, and VF measure electrocardiographic signals (ECG signals) which originates from a plurality of spatial positions on the surface of a human body 200. Hence, the electrodes VR, VL, and VF are located at different spatial positions, respectively. The channels 1182, 1184, 1186 capture ECG signals $S_1$, $S_2$ and $S_3$ from different spatial positions on the surface of the human body 200 by means of the electrodes VR, VL, and VF, respectively.

Figure 3A:
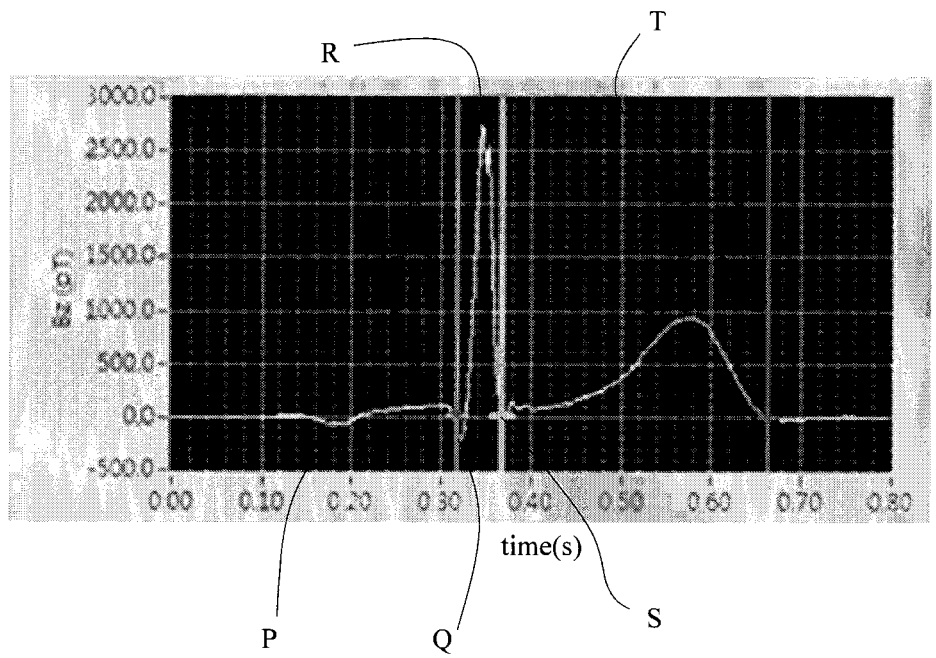
FIG. 3A is an electrocardiogram (ECG) at a spatial position and with a full cycle according to an embodiment of the present invention.
Figure 3B:
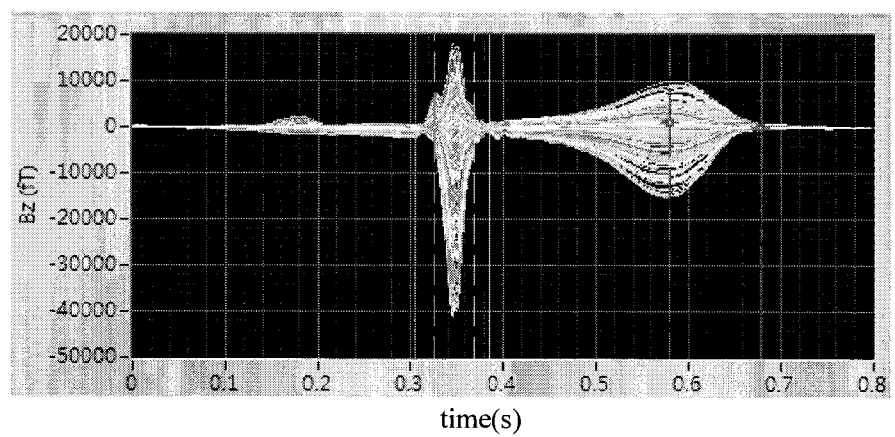
FIG. 3B is an electrocardiogram (ECG) at multiple spatial positions with a full cycle according to an embodiment of the present invention.

Referring to FIG. 1, FIG. 2, FIG. 3A and FIG. 3B, an electrocardiogram (ECG) at a spatial position and with a full cycle according to an embodiment of the present invention is shown in FIG. 3A, and an electrocardiogram (ECG) at multiple spatial positions with a full cycle according to an embodiment of the present invention is shown in FIG. 3B. As shown in the diagrams, the electrocardiographic signal measuring unit 110 retrieves and records the ECG signals $S_1$, $S_2$ and $S_3$ measured by channels 1182, 1184, 1186. As shown in the diagrams, the ECG signals each comprise P wave, Q wave, R wave, S wave, and T wave. The reconstruction unit 120 is electrically connected between the electrocardiographic signal measuring unit 110 and the parameter computation and assessment unit 130. The electrocardiographic signal measuring unit 110 comprises a signal buffer 112, an amplifier 113, and a filter 114. The amplifier 113 is electrically connected between the signal buffer 112 and the filter 114. The signal buffer 112 is electrically connected to the channels 1182, 1184, 1186 for receiving the ECG signals $S_1$, $S_2$ and $S_3$ retrieved by the electrodes VR, VL and VF (as shown in FIG. 2) at different spatial positions, respectively.

The signal buffer 112 protects the electrocardiographic signal measuring unit 110 against electrical surges. The signal buffer 112 provides an input impedance that is high enough to forward weak ECG signals measured on the human body surface to the amplifier 113. After receiving the ECG signals, the amplifier 113 amplifies them. The filter 114 eliminates protects the ECG signals by preventing baseline shift, reducing high-frequency noise, and blocking interference from power signals. The filter 114 operates at a band-pass frequency of 0.5 Hz~150 Hz and a band-stop frequency of 60 Hz. The electrocardiographic signal measuring unit 110 further comprises an analog-to-digital converter 115. The analog-to-digital converter 115 is electrically connected to the filter 114. The ECG signals are filtered by the filter 114 and then sent to the analog-to-digital converter 115 for conversion into digital signals for use in analysis and computation performed by the reconstruction unit 120 subsequently.

Figure 4:
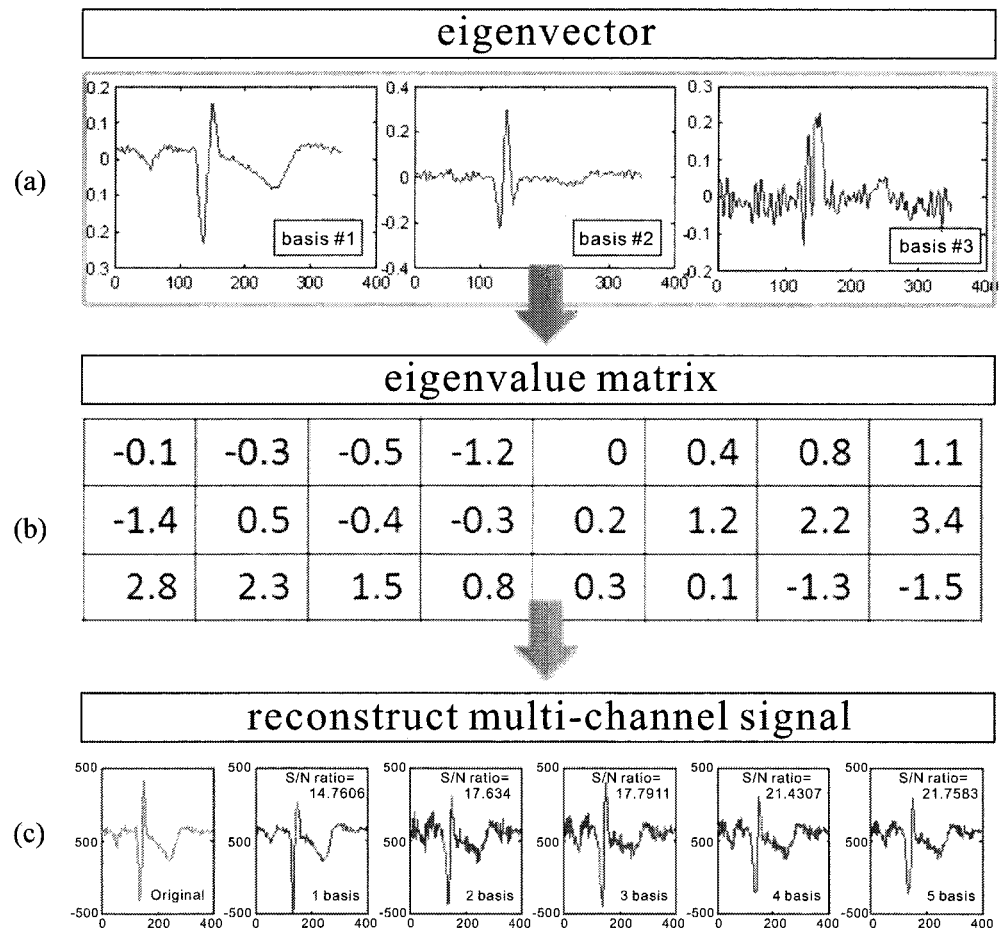
FIG. 4 is a schematic view of a process flow of a reconstruction algorithm according to an embodiment of the present invention.

Referring to FIG. 1 and FIG. 4, a schematic view of a process flow of a reconstruction algorithm according to an embodiment of the present invention is shown in FIG. 4. As shown in the diagrams, the reconstruction unit 120 comprises a reconstruction algorithm for calculating orthogonal eigenvectors $\phi$ of measured multi-channel ECG signals by principal component analysis (PCA), as shown in FIG. 4(a). With PCA, the ECG signals measured are expressed linearly in terms of variables independent of each other as follows:

$$X = k_1\phi_1 + k_2\phi_2 + k_3\phi_3 + \ldots + k_n\phi_n$$

where X denotes an original signal, $\phi$ denotes variables independent of each other, and k denote a variable weight coefficient for combining the variables linearly so as to express the original signal.

All the eigenvectors in a related matrix can be treated as a base to form matrix $\Phi$, where column vector $\phi_i$ is known as eigenvector.

$$\Phi = \begin{bmatrix} | & | & & | \\ \varphi_1 & \varphi_2 & \cdots & \varphi_L \\ | & | & & | \end{bmatrix};$$

$$\varphi_i = \begin{bmatrix} \varphi_i[0] \\ \varphi_i[1] \\ \vdots \\ \varphi_i[L-1] \end{bmatrix},$$

$$i = 1, 2 \ldots, L$$

$$X = \begin{bmatrix} | & | & & | \\ \varphi_1 & \varphi_2 & \cdots & \varphi_L \\ | & | & & | \end{bmatrix} \begin{bmatrix} k_1 \\ k_2 \\ \vdots \\ k_L \end{bmatrix} = \Phi k$$

Afterward, eigenvector $\psi_i$ is treated as a base for calculating an eigenvalue matrix k corresponding to channels at other different spatial positions, as shown in FIG. 4(b). Hence, k denotes a matrix that consists of related coefficients. Multi-channel ECG signals are treated as input signals and then decomposed by PCA into a polynomial, where every term is created by multiplying a PCA-enabled base with a coefficient related thereto. Then, with PCA, eigenvector significance is determined by the eigenvalue to select the most important eigenvector to function as the reconstruction base for reconstructing multi-channel ECG signals.

$$S_R = S^T * k,$$

$$S = \begin{bmatrix} | & | & & | \\ S_1 & S_2 & \cdots & S_k \\ | & | & & | \end{bmatrix},$$

$$S_i \in \varphi_i$$

Finally, the reconstruction unit 120 calculates a reconstructed ECG signal $S_R$ at the other different spatial positions with the eigenvalue matrix k and the ECG signals $S_1$, $S_2$ and $S_3$ of channels 1182, 1184, 1186 as shown in FIG. 4(c). The reconstructed ECG signal $S_R$ comprises a reconstructed P wave, a reconstructed Q wave, a reconstructed R wave, a reconstructed S wave, and a reconstructed T wave. The parameter computation and assessment unit 130 comprises a parameter computation and assessment algorithm. Due to differences in transmission direction and intrinsic impedance of the human body, different vector projections take place at the spatial positions of the channels in the course of the measurement of the ECG signals; as a result, periodic signals of different waveforms are captured. For example, a conventional 12-channel ECG is performed with six limb channels and six thoracic channels for providing signals specific to longitudinal cross-sections and transverse cross-sections of the heart.

The reconstruction algorithm of the reconstruction unit 120 is for use in calculating the eigenvalue matrix and the eigenvalues by means of the ECG signals measured with the electrodes VR, VL and VF. The product of the multiplication of the amplitude of the ECG signals of the channels and the eigenvalue matrix is used by the reconstruction algorithm of the reconstruction unit 120 to calculate indirectly a reconstructed ECG signal at the other different spatial positions, so as to overcome spatial resolution inadequacy and the lack of information required for analyzing and identifying signs and symptoms of diseases.

The parameter computation and assessment unit 130 comprises a parameter computation and assessment algorithm. Given an evaluation parameter $SI_{QTc}$, the parameter computation and assessment algorithm for the parameter $SI_{QTc}$ is:

$$SI_{QTc} = (1/S) \sum_S \left\{ (1/n) \sum_n |(QT_c)_k - (QT_c)_n| \right\},$$

where $SI_{QTc}$ denotes the degree of discreteness of the ECG signals $S_1$, $S_2$ and $S_3$ and the reconstructed ECG signal $S_R$, S denotes the total number of points of measurement of the ECG signals and the reconstructed ECG signals, k denotes a fixed spatial position, n denotes the number of points of measurement at the fixed spatial positions, and QTc denotes the interval of the ECG signals at the different spatial positions and a multi-dimension space defined by the reconstruction interval of the reconstructed ECG signals. The multi-dimension space QTc is defined by an interval QT from the Q wave to the T wave of the ECG signals and an interval QT from a reconstructed Q wave to a reconstructed T wave of the reconstructed ECG signals, and is calculated by the following equation:

$$QT_c = \frac{QT}{\sqrt{RR}},$$

where QT denotes the interval from the Q wave to the T wave of the ECG signals or the interval from the Q wave to the T wave of a reconstructed ECG signal, and RR denotes the interval between two adjacent R waves or the interval between two adjacent reconstructed R waves.

Figures 5A, 5B:
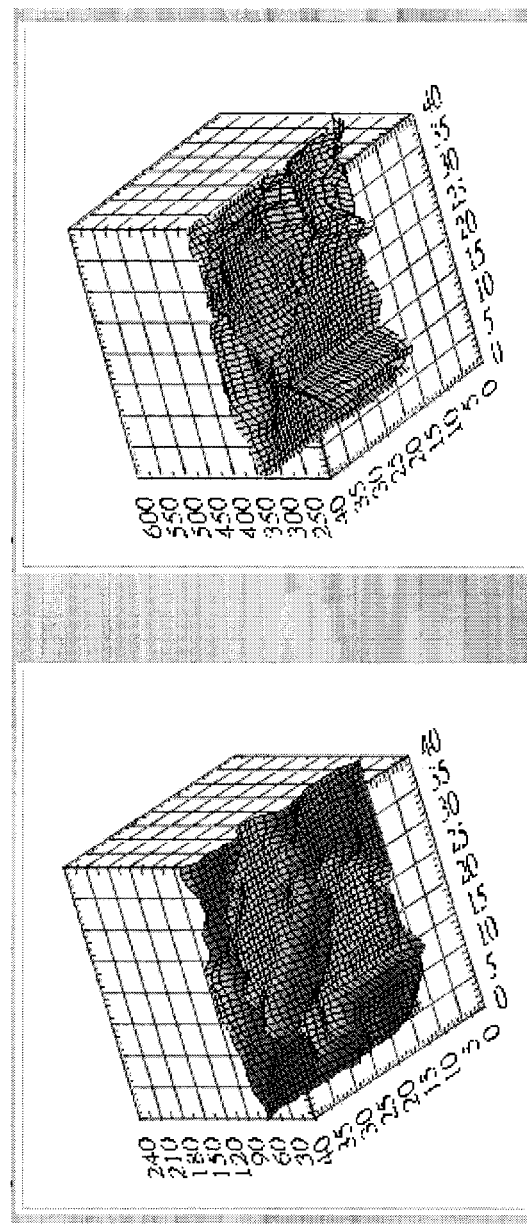
FIG. 5A is a schematic view of distribution of QTc at a spatial position under normal condition according to an embodiment of the present invention.
FIG. 5B is a schematic view of distribution of QTc at a spatial position under abnormal condition according to an embodiment of the present invention.

Referring to FIG. 5A and FIG. 5B, a schematic view of distribution of QTc at a spatial position under normal condition according to an embodiment of the present invention is shown in FIG. 5A, and a schematic view of distribution of QTc at a spatial position under abnormal condition according to an embodiment of the present invention is shown in FIG. 5B. As shown in the diagrams, the parameter computation and assessment unit 130 receives the ECG signals $S_1$, $S_2$ and $S_3$ measured with the channels 1182, 1184, 1186 of the electrocardiographic signal measuring unit 110, receives the at least one reconstructed ECG signal $S_R$ calculated by the reconstruction unit 120, calculates the starting point of the Q wave to the ending point of the T wave of the ECG signals, calculates the variation in the reconstruction interval from the starting point of the reconstructed Q wave to the ending point of the reconstructed T wave of the at least one reconstructed ECG signal against time at different spatial positions, and evaluates the degree of discreteness (i.e., $SI_{QTc}$) of the ECG signals $S_1$, $S_2$ and $S_3$ and the at least one reconstructed ECG signal $S_R$ with the parameter computation and assessment algorithm. The parameter computation and assessment unit 130 identifies an eigenvalue larger than a normal value according to $SI_{QTc}$, so as to determine whether the patient generating the ECG signals has a cardiovascular disease by making reference to the degree of discreteness $SI_{QTc}$. The parameter computation and assessment unit 130 calculates the variations of the T wave at different spatial positions with a T-wave propagation algorithm, so as to locate the lesion(s) of the cardiovascular disease.

In another embodiment, the electrocardiographic signal measuring unit 110 further comprises a communication unit 140 electrically connected to the electrocardiographic signal measuring unit 110, the reconstruction unit 120, and the parameter computation and assessment unit 130. The communication unit 140 is connected to a service platform 180 at a remote end through a network 170 by wireless or wired communication so as to send the ECG signals, reconstructed ECG signals, and data related to the degree of discreteness (i.e., $SI_{QTc}$) synchronously to the service platform 180 for use in medical services and distance diagnosis.

The reconstruction algorithm and the parameter computation and assessment algorithm of the present invention can be implemented by a physical circuit or software.

Figure 6:
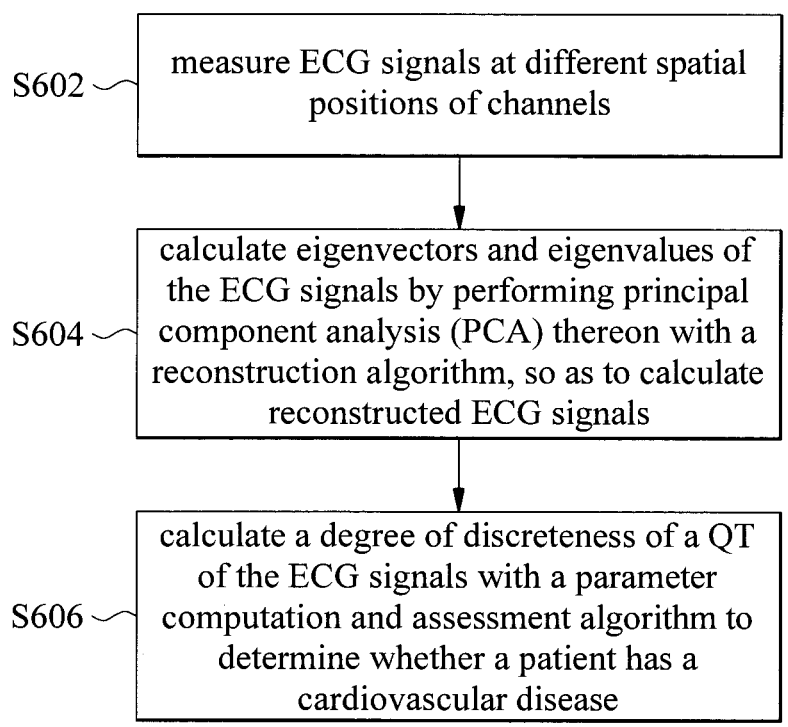
FIG. 6 is a flow chart of a method according to an embodiment of the present invention.

The second aspect of the present invention provides a method for evaluating cardiovascular performance in real time and characterized by conversion of a surface potential into multi-channels. Referring to FIG. 1 through FIG. 6, a flow chart of a method according to an embodiment of the present invention is shown in FIG. 6. The method is applicable to the system 100 for evaluating cardiovascular performance in real time as described above. Hence, the elements, structures, and circuits of the system 100 for evaluating cardiovascular performance in real time are not described again below for the sake of brevity. The method for evaluating cardiovascular performance in real time comprises the steps as follows:

Step S602: measuring the ECG signals $S_1$, $S_2$ and $S_3$ at different spatial positions with channels 1182, 1184 and 1186 by the electrocardiographic signal measuring unit 110, wherein the ECG signals each comprise P wave, Q wave, R wave, S wave, and T wave.

Step S604: calculating orthogonal eigenvectors of measured multi-channel ECG signals by performing principal component analysis (PCA) thereon with a reconstruction algorithm by the reconstruction unit 120, and calculating an eigenvalue matrix by using the eigenvectors as a base.

The reconstruction unit 120 calculates and reconstructs at least one reconstructed ECG signal $S_R$ at the other different spatial positions with the eigenvalue matrix and the ECG signals $S_1$, $S_2$ and $S_3$ of the channels 1182, 1184 and 1186. The reconstructed ECG signal $S_R$ comprises a reconstructed P wave, a reconstructed Q wave, a reconstructed R wave, a reconstructed S wave, and a reconstructed T wave.

Step S606: receiving, by the parameter computation and assessment unit 130, the ECG signals $S_1$, $S_2$ and $S_3$ measured by the electrocardiographic signal measuring unit 110 and the reconstructed ECG signal $S_R$ calculated by the reconstruction unit 120, calculating the interval from the starting point of the Q wave to the ending point of the T wave of the ECG signals $S_1$, $S_2$ and $S_3$, calculating variation in the reconstruction interval from the starting point of a reconstructed Q wave to the ending point of a reconstructed T wave of the reconstructed ECG signal $S_R$ against time at different spatial positions, and evaluating the degree of discreteness of the ECG signals $S_1$, $S_2$ and $S_3$ and the at least one reconstructed ECG signal $S_R$ with a parameter computation and assessment algorithm to determine whether the patient has a cardiovascular disease.

The present invention uses a reconstruction algorithm in enhancing spatial resolution of ECG signals by means of multi-channel ECG signals measured at different spatial positions, and uses a parameter computation and assessment algorithm to evaluate cardiovascular performance, so as to locate the lesions of cardiovascular diseases and evaluate cardiovascular performance in real time.

The present invention is disclosed above by preferred embodiments. However, persons skilled in the art should understand that the preferred embodiments are illustrative of the present invention only, but should not be interpreted as restrictive of the scope of the present invention. Hence, all simple equivalent variations and modifications made to the aforesaid embodiments should fall within the scope of the present invention. Accordingly, the legal protection for the present invention should be defined by the appended claims.

The claims are as follows:

1. A system for evaluating cardiovascular performance in real time and characterized by conversion of a surface potential into multi-channels, the system comprising:

an electrocardiographic signal measuring unit comprising at least one channel located at different spatial positions, the electrocardiographic signal measuring unit recording electrocardiographic signals (ECG signals) measured with the channels, the ECG signals each comprising a P wave, a Q wave, a R wave, a S wave, and a T wave;

a reconstruction unit electrically connected to the electrocardiographic signal measuring unit, the reconstruction unit having a reconstruction algorithm for calculating eigenvectors of the ECG signals and using the eigenvectors as a base for calculating an eigenvalue matrix, the reconstruction unit calculating at least one reconstructed ECG signal at other different spatial positions with the eigenvalue matrix and the ECG signals of the channels, the at least one reconstructed ECG signal comprising a reconstructed P wave, a reconstructed Q wave, a reconstructed R wave, a reconstructed S wave, and a reconstructed T wave; and a parameter computation and assessment unit electrically connected to the reconstruction unit and having a parameter computation and assessment algorithm, wherein the parameter computation and assessment unit receives the ECG signals and the at least one reconstructed ECG signal, calculates an interval from a starting point of the Q wave to an ending point of the T wave of the ECG signals, calculates variation in a reconstruction interval from a starting point of the reconstructed Q wave to an ending point of the reconstructed T wave of the at least one reconstructed ECG signal against time at different spatial positions, and evaluates the degree of discreteness of the ECG signals and the at least one reconstructed ECG signal with the parameter computation and assessment algorithm;

wherein the parameter computation and assessment algorithm is: $SI_{QTc}=(1/S)$ $$SI_{QTc} = (1/S) \sum_S \left\{ (1/n) \sum_n |(QT_c)_k - (QT_c)_n| \right\},$$

wherein $SI_{QTc}$ denotes the degree of discreteness of the ECG signals and the at least one reconstructed ECG signal, S denotes a total number of points of measurement of the ECG signals and the at least one reconstructed ECG signal, k denotes a fixed spatial position, n denotes a number of points of measurement most proximate to the fixed spatial position, and $QT_c$ denotes a multi-dimension space defined by the interval of the ECG signals and the reconstruction interval of the at least one reconstructed ECG signal.

2. The system for evaluating cardiovascular performance in real time of claim 1, wherein a multi-dimension space defined by an interval of the ECG signals and a reconstruction interval of the at least one reconstructed ECG signal is calculated by equation:

$$QT_c = \frac{QT}{\sqrt{RR}},$$

wherein QT denotes the interval or the reconstruction interval, and RR denotes the interval between two adjacent R waves or the interval between two adjacent reconstructed R waves.

3. The system for evaluating cardiovascular performance in real time of claim 1, wherein the electrocardiographic signal measuring unit further comprises a signal buffer, an amplifier, and a filter, the signal buffer being electrically connected to the channels for receiving the ECG signals measured with the channels and protecting the electrocardiographic signal measuring unit, the amplifier being electrically connected between the signal buffer and the filter for receiving and amplifying the ECG signals, and the filter filtering out interference noise of the ECG signals.

4. The system for evaluating cardiovascular performance in real time of claim 1, further comprising a communication unit electrically connected to the electrocardiographic signal measuring unit, the reconstruction unit, and the parameter computation and assessment unit, the communication unit being connected to a service platform at a remote end by means of wireless or wired communication for transmitting the ECG signals, the at least one reconstructed ECG signal, and data related to the degree of discreteness thereof synchronously.

5. The system for evaluating cardiovascular performance in real time of claim 1, wherein the reconstruction algorithm is implemented by a physical circuit.

6. The system for evaluating cardiovascular performance in real time of claim 1, wherein the parameter computation and assessment algorithm is implemented by a physical circuit.

7. The system for evaluating cardiovascular performance in real time of claim 1, wherein the parameter computation and assessment unit determines whether the ECG signals are attributable to a cardiovascular disease based on the degree of discreteness.

8. A method for evaluating cardiovascular performance in real time and characterized by conversion of a surface potential into multi-channels, the method comprising the steps of:
measuring, by the electrocardiographic signal measuring unit, electrocardiographic signals (ECG signals) at different spatial positions with at least one channel, the ECG signals each comprising a P wave, a Q wave, a R wave, a S wave, and a T wave;
calculating, by a reconstruction unit, eigenvectors of the ECG signals with a reconstruction algorithm, an eigenvalue matrix with the eigenvectors being used as a base, and at least one reconstructed ECG signal at other different spatial positions with the eigenvalue matrix and the ECG signals of the channels, the at least one reconstructed ECG signal comprising a reconstructed P wave, a reconstructed Q wave, a reconstructed R wave, a reconstructed S wave, and a reconstructed T wave; and
receiving the ECG signals and the at least one reconstructed ECG signal by a parameter computation and assessment unit, calculating an interval from a starting point of the Q wave to an ending point of the T wave of the ECG signals, calculating variation in a reconstruction interval from a starting point of a reconstructed Q wave to an ending point of a reconstructed T wave of the at least one reconstructed ECG signal against time at different spatial positions, and evaluating a degree of discreteness of the at least one reconstructed ECG signal and the ECG signals with the parameter computation and assessment algorithms;

wherein the parameter computation and assessment algorithm is: $SI_{QTc} = (1/S)$ $$SI_{QTc} = (1/S) \sum_{S} \left\{ (1/n) \sum_{n} |(QT_c)_k - (QT_c)_n| \right\},$$

wherein $SI_{QTc}$ denotes the degree of discreteness of the ECU signals and the at least one reconstructed ECG signal, S denotes a total number of points of measurement of the ECG signals and the at least one reconstructed ECG signal, k denotes a fixed spatial position, n denotes a number of points of measurement most proximate to the fixed spatial position, and $QT_c$ denotes a multi-dimension space defined by the interval of the ECG signals and the reconstruction interval of the at least one reconstructed ECG signal.

9. The method for evaluating cardiovascular performance in real time of claim 8, wherein a multi-dimension space defined by the interval of the ECG signals and the reconstruction interval of the at least one reconstructed ECG signal is calculated by equation:

$$QT_c = \frac{QT}{\sqrt{RR}},$$

wherein QT denotes the interval or the reconstruction interval, and RR denotes the interval between two adjacent R waves or the interval between two adjacent reconstructed R waves.

10. The method for evaluating cardiovascular performance in real time of claim 8, wherein the electrocardiographic signal measuring unit further comprises a signal buffer, an amplifier, and a filter, the signal buffer being electrically connected to the channels for receiving the ECG signals measured with the channels and protecting the electrocardiographic signal measuring unit, the amplifier being electrically connected between the signal buffer and the filter for receiving and amplifying the ECG signals, and the filter filtering out interference noise of the ECG signals.

11. The method for evaluating cardiovascular performance in real time of claim 8, wherein a communication unit is electrically connected to the electrocardiographic signal measuring unit, the reconstruction unit, and the parameter computation and assessment unit, the communication unit being connected to a service platform at a remote end by means of wireless or wired communication for transmitting the ECG signals, the at least one reconstructed ECG signal, and data related to the degree of discreteness thereof synchronously.

12. The method for evaluating cardiovascular performance in real time of claim 8, wherein the reconstruction algorithm is implemented by a physical circuit.

13. The method for evaluating cardiovascular performance in real time of claim 8, wherein the parameter computation and assessment algorithm is implemented by a physical circuit.

14. The method for evaluating cardiovascular performance in real time of claim 8, wherein the parameter computation and assessment unit determines whether the ECG signals are attributable to a cardiovascular disease based on the degree of discreteness.

* * * * *